United States Patent
Raphael et al.

(10) Patent No.: US 8,505,533 B2
(45) Date of Patent: Aug. 13, 2013

(54) DETECTION AND SUPPRESSION OF AIRWAY / DRAPE FIRES DURING SURGICAL PROCEDURES

(75) Inventors: David T. Raphael, Valley Village, CA (US); Paul Ronney, Monrovia, CA (US)

(73) Assignee: University of Southern California, Los Angeles, CA (US)

( * ) Notice: Subject to any disclaimer, the term of this patent is extended or adjusted under 35 U.S.C. 154(b) by 415 days.

(21) Appl. No.: 12/789,085

(22) Filed: May 27, 2010

(65) Prior Publication Data

US 2010/0300708 A1    Dec. 2, 2010

Related U.S. Application Data

(60) Provisional application No. 61/181,952, filed on May 28, 2009.

(51) Int. Cl.
*A61M 16/04* (2006.01)
*A61M 16/00* (2006.01)
*A62C 3/00* (2006.01)
*A62C 37/11* (2006.01)

(52) U.S. Cl.
USPC ............ 128/202.24; 128/202.22; 128/207.14; 169/54; 169/60

(58) Field of Classification Search
USPC ................ 169/45, 46, 54, 56, 60, 61, 70, 91; 128/207.14–207.17, 202.22, 202.24; 606/32–34, 41, 42, 46, 49
See application file for complete search history.

(56) References Cited

U.S. PATENT DOCUMENTS

| | | | |
|---|---|---|---|
| 4,569,341 A | | 2/1986 | Morris |
| 4,622,965 A | * | 11/1986 | Teeple ...................... 128/207.14 |
| 5,027,812 A | | 7/1991 | Shapiro et al. |
| 5,040,531 A | * | 8/1991 | Coleman et al. ......... 128/207.14 |
| 5,042,476 A | | 8/1991 | Smith |
| 5,078,131 A | * | 1/1992 | Foley ........................ 128/203.15 |
| 6,181,250 B1 | * | 1/2001 | Brooks, Jr. ..................... 340/577 |
| 6,382,207 B1 | | 5/2002 | Giuffre et al. |
| 7,291,145 B2 | | 11/2007 | Seid |

(Continued)

OTHER PUBLICATIONS

International Search Report and Written Opinion of the International Searching Authority (Korean Intellectual Property Office), mailed Jan. 25, 2011, for PCT Application No. PCT/US2010/036416, filed May 27, 2010 (International Application corresponding to U.S. Appl. No. 12/789,085).

(Continued)

*Primary Examiner* — Darren W Gorman
(74) *Attorney, Agent, or Firm* — McDermott Will & Emery LLP

(57) ABSTRACT

Apparatus for oxygenating the airway of a patient may include a device for delivering an oxygen-carrying gas into the airway, a fire detection system configured to detect indications of an imminent or incipient fire in the airway, and a fire suppression system configured to suppress the imminent or incipient fire in the airway in response to detection of the fire in the airway by the fire detection system.

A drape for use during surgery on a patient may include a sheet configured to cover an area of the patient during surgery, a fire detection system attached to the sheet and configured to detect indications of an imminent or incipient fire beneath the sheet, and a fire suppression system attached to the sheet and configured to suppress the imminent or incipient fire beneath the sheet in response to detection of the imminent or incipient fire by the fire detection system.

12 Claims, 7 Drawing Sheets

(56) References Cited

U.S. PATENT DOCUMENTS

| | | | |
|---|---|---|---|
| 7,296,571 B2 | 11/2007 | Foltz et al. | |
| 2004/0226725 A1* | 11/2004 | Bennett | 169/44 |
| 2006/0058784 A1* | 3/2006 | Gedebou | 606/45 |
| 2006/0069387 A1 | 3/2006 | Gaedebou et al. | |

OTHER PUBLICATIONS

American Society of Anesthesiologists Task Force on Operating Room Fires. 2008. Practice Advisory for the Prevention and Management of Operating Room Fires. Anesthesiology, May 2008, vol. 108, pp. 786-801.

Bailey, M. K. et al. 1990. Electrocautery-Induced Airway Fire During Tracheostomy. Anesth Analg. 1990, vol. 71, pp. 702-704.

Bowdle, T. A. et al. 1987. Fire Following Use of Electrocautery During Emergency Percutaneous Transtracheal Ventilation. Anesthesiology, May 1987, vol. 66, No. 5, pp. 697-698.

Chen, S.-J. et al. 2007. Fire Detection Using Smoke and Gas Sensors. Fire Safety Journal, 2007, vol. 42, pp. 507-515.

Cozine, K. et al. 1981. Laser-Induced Endotracheal Tube Fire. Anesthesiology, Nov. 1981, vol. 55, No. 5, pp. 583-585.

Dyer, R.F. et al. 1976. Polyvinyl Chloride Toxicity in Fires: Hydrogen Chloride Toxicity in Fire Fighters. JAMA, Jan. 26, 1976, vol. 235, No. 4, pp. 393-397, 1689.

Gottuk, D.T. et al. 2002. Advanced Fire Detection Using Multi-Signature Alarm Algorithms. Fire Safety Journal 2002, vol. 37, pp., 381-394. (Note: Paper presented at AUBE '99 (11th International Conference on Automatic Fire Detection, Duisburg, Mar. 16-18, 1999).

Hinderer, R.K. et al. 1989. Update on Smoke Toxicity of Vinyl Compounds. Journal of Vinyl Technology, Jun. 1989, vol. 11, No. 2, pp. 50-58.

Kallonen, R. 1990. Smoke Gas Analysis by FTIR Method: Preliminary Investigation. Journal of Fire Sciences, Sep.-Oct. 1990, vol. 8, pp. 343-360.

Kaplan, H.L. et al. 1993. Acute and Long-Term Effects of Polyvinylchloride (PVC) Smoke on the Respiratory System of the Baboon and a Comparison with the Effects of Hydrogen Chloride (HCl). Journal of Fire Sciences, Nov.-Dec. 1993, vol. 11, pp. 485-511.

Pasternak, M. et al. 1982. Studies of the Chemical Mechanism of Smoke Particulates Formation During the Combustion of Chlorinated Polymers. Combustion Science and Technology, 1982, vol. 28, pp., 263-270.

Rita, L. et al. 1982. Endotracheal Tube Ignition During Laryngeal Surgery with Resectoscope. Anesthesiology, Jan. 1982, vol. 56, pp. 60-61.

Simpson, J.I. et al. 1986. Endotracheal Tube Fire Ignited by Pharyngeal Electrocautery. Anesthesiology, Jul. 1986, vol. 65, pp. 76-77.

Singla, A.K. et al. 2005. Surgical Field Fire During a Repair of Bronchoesophageal Fistula. Anesth Analg., 2005, vol. 100, pp. 1062-1064.

Sosis, M.B. 1990. Airway Fire During CO2 Laser Surgery Using a Xomed Laser Endotracheal Tube. Anesthesiology, Apr. 1990, vol. 72, No. 4, pp. 747-749.

Weber, S.M. et al. 2006. DuraPrep and the Risk of Fire During Tracheostomy. Head and Neck—DOI 10.1002/hed, Jul. 2006, pp. 649-652.

Wolf, G.L. et al. 1987. Flammability of Endotracheal Tubes in Oxygen and Nitrous Oxide Enriched Atmosphere. Anesthesiology, Aug. 1987, vol. 67, No. 2, pp. 236-239.

* cited by examiner

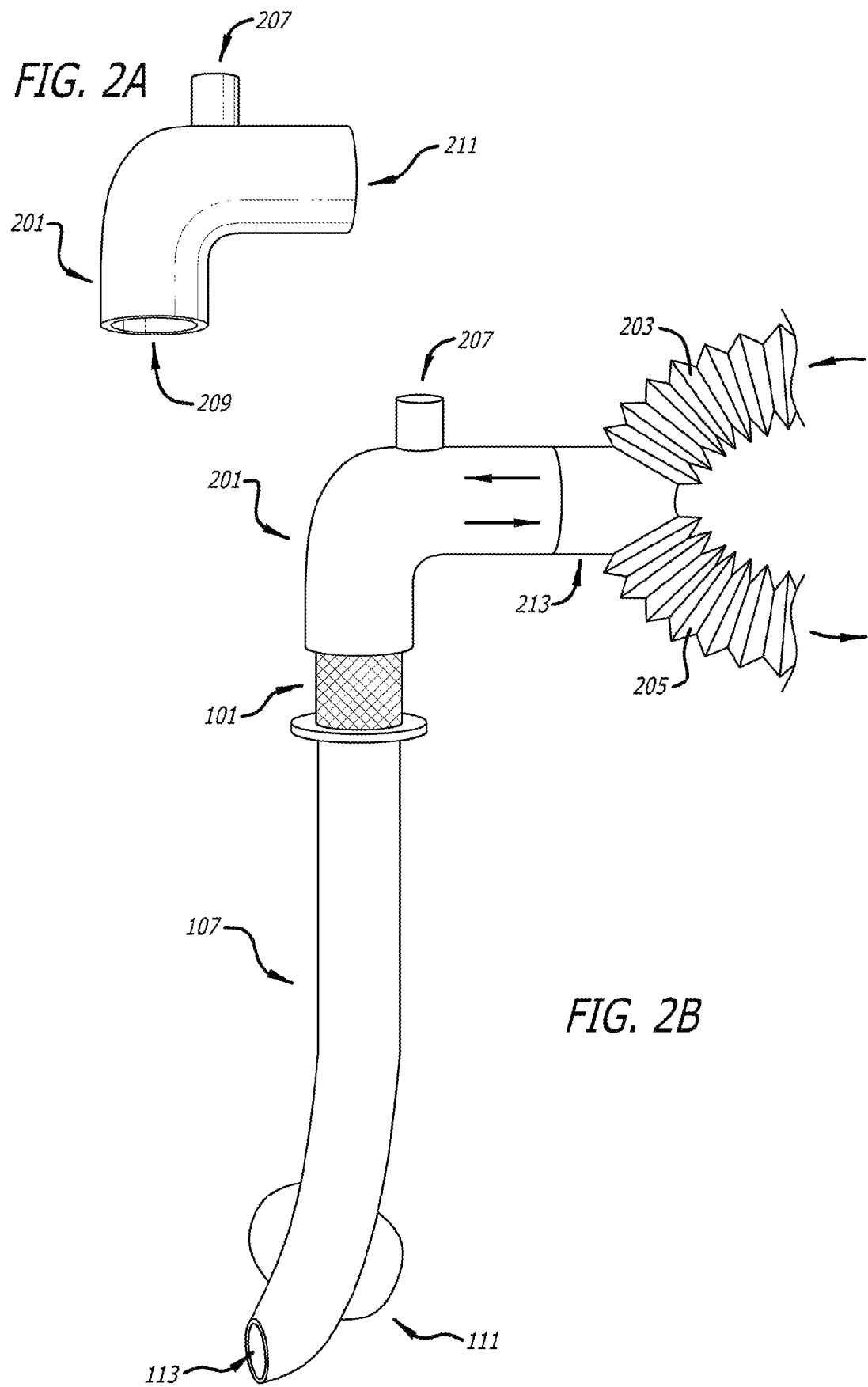

DETECTION AND SUPPRESSION OF AIRWAY / DRAPE FIRES DURING SURGICAL PROCEDURES

CROSS-REFERENCE TO RELATED APPLICATION

This application is based upon and claims priority to U.S. Provisional Patent Application No. 61/181,952, entitled "DEVICE FOR AIRWAY FIRES," filed May 28, 2009. The entire content of this application is incorporated herein by reference.

BACKGROUND

1. Technical Field

This disclosure relates to undesirable airway and drape fires which may erupt during surgical procedures.

2. Description of Related Art

Dangerous fires can and do occur during surgery, including in patient airways and under surgical drapes.

An airway fire is a fire in the airway or breathing circuit of a patient. Airway fires may be low-frequency, peri-anesthetic adverse events that may occur in healthy patients with devastating consequences, including severe burns, disfigurement, and death. Studies have established that incendiary characteristics and breakdown products of polyvinyl chloride (PVC) endotracheal tubes (ETTs), as well as the clinical scenarios, can lead to an airway or surgical field fire.

In a closed-claims review by an American Society of Anesthesiologists (ASA) Committee, the number of operating room (O.R.) fires was estimated to be between 50 to 200 operating room fires per year, with as many as 20% of the reported fires resulting in serious injury or death. However, the ECRI Institute, a nonprofit health services research organization, in collaboration with the Anesthesia Patient Safety Foundation, has reported that the estimate is more correctly between 500-650 cases of operating room fires per year. Because of medico-legal reasons, many fires may not be reported in the open literature. Thus, the true incidence may likely be higher.

As an example, one operating room fire occurred during an attempted Burr Hole procedure in a patient receiving 6 L $O_2$ per minute through a face mask. Upon activation of a monopolar electrocautery surgical unit (ESU), a muffled 'pop' was heard, followed by the appearance of smoke under the drapes. When the drape was removed, the patient's head was reportedly engulfed in a "ball of flame." The oxygen mask was also observed to be in flames. The fire was extinguished within 15 seconds. Still, the patient sustained second degree burns to the face, neck, and upper chest, complicated by pneumonia and a two-month hospitalization. The sequence of events leading to the fire was simulated with a manikin. The causes of the fire were considered to be threefold: ESU ignition, an enriched oxygen environment provided by the face mask in a tented closed space, and fuel provided by vapors from an alcohol-based preparation solution.

Fire Sources in the Operating Room

Three elements must usually be present for a fire: an ignition source, an oxidizer, and a fuel source. The categorical causes may be broadly described as:

Ignition sources in the O.R. setting include electrocautery, electrosurgical units, lasers, heated probes, drills or burrs (heat or sparks), argon beam collimators, fiber-optic light cables, defibrillation pads or paddles, and other heat-generating or flame-generating devices.

Gaseous oxidizers include oxygen and nitrous oxide, the latter being a potent oxidizer. Oxidizer enriched environments can be created internally within a closed or semi-closed (circle system) breathing circuit, the endotracheal tube (ETT)/laryngeal mask airway (LMA), the lower airway below the vocal cords, and in any breathing tube that serves as a conduit for delivery of oxygen to the lungs. Other oxygen delivery systems in use include tracheostomy tubes, double-lumen tubes for separate and/or combined lung ventilation, transtracheal oxygen jet devices, and endoscopes equipped with channels for gas delivery. An oxidizer-rich environment can also be created externally with the use of open gas sources (e.g., nasal cannulae, external face masks, tracheostomy masks), particularly when combined with drapes and tenting environments that promote the pooling of oxygen or nitrous oxide.

Potential fuel sources include (1) Patient: hair, gastrointestinal gases; (2) Surgical preparation agents: alcohol, degreasers (acetone), aerosols, tinctures (benzoin, mastazol), ethyl chloride spray, dermatone glue; (3) Linens: gowns, drapes, blankets, paper materials; (4) Dressings: stockinette, tapes, sponges, collodion, gauze; (5) Ointments: wax, medical adhesive spray, petrolatum, tincture of benzoin, plastic and rubber products; (6) Anesthesia components: Breathing/respiratory circuits, mask, airways, ETTs, carbon dioxide absorbents. Flammable agents (ether) are no longer used in the USA and other modern countries.

With use of an ETT, there are two possible regions within which an airway fire can originate—either within the ETT lumen, or external to the ETT. Airway fires can occur even without an ETT, such as with nasal cannulas and face masks.

For surgery cases requiring a sterile cover sheet, an ignitable environment can be created in a closed tented space underneath the sheet. This scenario can arise in multiple ways, such as when (a) an oxygen-enriched space is created underneath the sheet with supplementary oxygen given to a non-intubated patient, or (b) when there is an accumulation of ignitable vapors from incompletely dried surgical prep solutions. Many other potential fire scenarios exist.

Fire Prevention and the ASA Response Algorithm

The International Organization for Standardization, Anesthesia Patient Safety Foundation, and the American Society of Anesthesiologists (ASA) have developed educational programs to minimize the incidence of OR fires, and to improve the quality and speed of the OR team response. If an airway fire erupts, for example, the ASA algorithm requires the following: the ETT is immediately removed, the flow of airway gases is stopped, flammable materials are removed, and a bowl of saline is poured into the airway.

However, a sudden outburst of fire may startle most individuals. Despite prior drills, the instinctive response of a team member may be to back away initially from the danger. Seconds can matter in an airway burn, and it may take seconds for the anesthesiologist to turn off the oxygen, remove the tape, and pull out the ETT which may be on fire. The saline may not have been poured into a vessel, or could be spilled, thus making it unavailable for use by the surgeon.

Flame Spread in Tracheal Tubes

Upon ignition of a tracheal tube, there are three types of flames that can occur: (1) extraluminal outer surface flames that can arise when the $O_2$ concentration outside the tube exceeds the $O_2$ flammability index, (2) intraluminal upstream flames and (3) intraluminal downstream flames.

Model studies have demonstrated that, when the free distal end of an ETT is ignited by a pilot flame, if the $O_2$ concentration is sufficiently high, an intraluminal upstream flame develops and spreads against the direction of the oxygen flow toward the supply of oxidizer at the proximal end of the tube. The flame may spread at a speed of 1.5 to 2 cm/sec at $O_2$ flow rates of 2-5 liters/min.

A third type of flame, the intraluminal downstream flame, feeds off the excess un-reacted gaseous fuel generated by the upstream flame. It is this downstream flame anchored distally that is regarded as the most dangerous.

In general, extraluminal flames tend to be mild, while intraluminal (and particularly downstream) flames can be violent owing to the forced supply of oxidizer with high $O_2$ concentration and high total flow rates. When a laser beam strikes the outside wall of an ETT, an extraluminal fire can be created, and with penetration through the wall, an intraluminal flame as well.

Vulnerability of Laser Shields

Several manufacturers have designed tracheal tubes to be resistant to the effects of a laser, such as the Laser-Shield II tracheal tube, Norton tube, Lasertubus, and Sheridan Laser Trach Tube. However, each may have limitations. In an earlier version of the silicone-based Xomed Laser Shield ETT (externally coated with a layer of metal particles), for example, the shaft of the Xomed ETT in a 100% environment could be ignited with long-term exposure to a laser beam, with conversion into an intense "blowtorch." The Laser-Flex ETT has a stainless steel shaft, but has a large outer diameter (difficult to use in small patients and children), small inner diameter (may limit ventilatory flow), and a vulnerable cuff. If the tube wall is heated above 160 degrees C., 'hot spots' may develop and the inner PVC cuff conduits may begin to disintegrate and can be ignited with Nd—YAG lasers.

The Non-Intubated Airway—A Standardized Protective Tent

For monitored anesthesia care not involving an ETT, supplementary $O_2$ may be provided by a face mask or nasal cannula. With drapes over the patient's head, a tenting effect is created, and excess $O_2$ gas may accumulate, particularly in drape folds, thus producing an ignitable environment. A high-energy laser beam can ignite the drape, and can ignite the underlying $O_2$-enriched airway mask/cannula/anesthesia tubing, the patient's hair or clothing, or the bed linen.

The Emergency Care Research Institute (ECRI) reports that 60% of operating room fires involve a surgical drape as fuel and 40% occur in an oxygen-enriched environment. New drape materials made of polypropylene or phenol polymer may not ignite in air for 30 seconds in the presence of a 15 W carbon dioxide laser beam. However, a small hole may be created through the drape, which may secondarily ignite flammable material placed underneath it.

Further, there is no surgical drape material, either currently available or proposed, that is not ignitable in a 50% or 95% $O_2$ environment.

SUMMARY

Apparatus for oxygenating the airway of a patient may include a device for delivering an oxygen-carrying gas into the airway, a fire detection system configured to detect indications of an imminent or incipient fire in the airway, and a fire suppression system configured to suppress the imminent or incipient fire in the airway in response to detection of the imminent or incipient fire in the airway by the fire detection system.

The device for delivering an oxygen-carrying gas may be an endotracheal tube, a laryngeal mask airway, or any other breathing tube that serves as a conduit for delivery of oxygen to the lungs. The fire detection system may be configured to detect indications of an imminent or incipient fire within the lumen of the endotracheal tube/oxygen-carrying breathing tube. The fire suppression system may be configured to suppress the imminent or incipient fire within the lumen of the endotracheal tube/oxygen-carrying breathing tube in response to detection of the imminent or incipient fire in the lumen of the endotracheal tube/oxygen-carrying breathing tube by the fire detection system.

An endotracheal tube/breathing tube may have an inserted adapter at the proximal end of the tube. The adapter may have two ends. A distal end may insert into the lumen of the tube. This distal end may be inner-diameter (I.D.)—specific, i.e., the distal adapter end may have approximately the same inner diameter as the ETT/breathing tube. The proximal end of the adapter may have a standardized 15 mm diameter male fitting, which may connect to the breathing circuit connector. The breathing circuit connector may be interposed between the adapter and the breathing circuit. The shape of the breathing circuit connector may be straight, be of variable angle, may be elbow-shaped in the form of a right-angle bend, or may be of another shape. The connector may serve as an intermediate conduit for delivery and passage of oxygen-carrying gas from the breathing circuit to and through the ETT/breathing tube to the lungs, and then back from the ETT/breathing tube to the breathing circuit.

Attached to the ETT/breathing tube male connector may be a 22 mm diameter female fitting of a manual ventilation bag or of an automatic anesthesia/ICU ventilation/system. There may be one or more multiple connectors of different shapes (straight, variable angle, and right angle) between the ventilation system and the ETT/breathing tube. For example, within a circle anesthesia ventilation system, there may be a Y-piece with two 22 mm male ports for connection to the ETT/breathing tube. Other ventilation systems with the same standardized fittings, including coaxial tube systems, may include the Mapleson A, B, C, D, E, and F ventilation systems.

The endotracheal tube may include an elongated tube or connector piece at the other end of the elbow having a longitudinal axis which may make an approximately 90 degree angle with respect to the longitudinal axis of the gas inlet. This may align the axis of the proximal ETT lumen with the axis of the right angle connector and may improve the quality of gas collection and sampling. The fire detection and suppression systems may both be configured to receive access to the lumen of the elongated tube or connector piece at approximately the bend of the elbow.

The fire detection system may be configured to detect indications of an imminent or incipient fire outside of the ETT/breathing tube. The fire suppression system may be configured to suppress the imminent or incipient fire outside of the ETT/breathing tube in response to detection of the imminent or incipient fire outside of the ETT/breathing tube by the fire detection system.

The fire detection system may include a thermistor embedded in the outer wall of the ETT/breathing tube. The thermistor may include a set of spaced-apart and stacked rings of thermistor wire.

The fire suppression system may include a plurality of fluid outlets spaced from one another along a length and circumference of the outer wall of the ETT/breathing tube.

The fire suppression system may be configured to suppress the imminent or incipient fire in the airway associated with the interior lumen of the ETT/breathing tube by injecting a blast of non-flammable gas, or by injecting a jet of liquid saline or other fire suppressant, into the airway associated with the interior lumen of the ETT/breathing tube in response to detection of the imminent or incipient fire in the airway by the fire detection system.

The fire detection system may be configured to detect one or more of the following within the airway associated with the interior lumen of the ETT/breathing tube: a rapid change in temperature, a flame, an ignitable atmosphere, ignitable vapors, combustion byproducts, toxic material, and smoke. The fire detection system may use Fourier Transform Infrared Spectroscopy to detect at least one of these listed parameters.

A drape for use during surgery on a patient may include a sheet configured to cover an area of the patient during surgery, a fire detection system attached to the sheet and configured to detect indications of an imminent or incipient fire beneath the sheet, and a fire suppression system attached to the sheet and configured to suppress the imminent or incipient fire beneath the sheet in response to detection of the imminent or incipient fire by the fire detection system.

The fire detection system may include a grid of thermistor wire underneath and spanning across at least a substantial portion of the area covered by the sheet.

The fire detection system may include a grid of gas sampling inlets underneath and spanning across at least a substantial portion of the area covered by the sheet. The gas sampling inlets may be connected to a common conduit that delivers the gas samples to a Fourier Transform Infrared Spectroscopy (FTIR) data collection/data processing unit. There may be a steady flow of air through the gas sampling inlets, in possible conjunction with a suctioning device, to provide continuous delivery of the gas samples to the FTIR processing unit.

The fire detection system may include a manifold consisting of a horizontal array of tubes with multiple holes in them, such that the steady flow of air, in possible conjunction with a suctioning device, is collected into a common conduit that provides continuous delivery of the gas samples to the FTIR processing unit. The manifold grid of holes may serve as gas sampling inlets that are underneath and span across at least a substantial portion of the area covered by the sheet. The manifold may be made from a temperature-resistant Vespel polyimide plastic (melting point 500 degrees C.) or other like plastic.

The fire detection system may include a porous spongy like material, such as open cell foam, that through its pores allows gas samples to be collected into a common non-porous common conduit that provides continuous delivery of the gas samples to the FTIR processing unit. The pores of the spongy material may serve as gas sampling inlets that are underneath and span across at least a substantial portion of the area covered by the sheet. The spongy material may be made of a deformable temperature-resistant polyimide or other like plastic.

The fire detection system may include a pancake-like chamber underneath and spanning across at least a substantial portion of the area covered by the sheet. The pancake-like chamber may contain a marker gas configured to leak from a breach in the pancake-like chamber caused by heat or fire and to be detected by at least one of the sampling inlets near the breach.

The fire detection system may include another pancake-like chamber underneath and spanning across at least a substantial portion of the area covered by the sheet. The pancake-like chamber may contain fire-suppressing material that, upon a breach of the pancake-like chamber caused by fire or heat, leaks from the pancake-like chamber at the location of the breach, thereby suppressing the imminent or incipient fire beneath the sheet.

For structural support, the fire detection system may include a series of evenly spread box springs that are distributed across at least a substantial portion of the area covered by the sheet. The box springs may serve as struts to create an open chamber between the gas sampling inlet system and the underlying pancake-like chamber containing the fire-suppressing material. Gas samples may be collected from this open chamber.

For structural support, the fire detection system may include a manifold of evenly spread horizontal tubes, each with multiple holes that allow gas samples to be collected. The horizontal tube system may serve as a supportive strut by which to create an open chamber between the gas sampling inlet system and between the underlying pancake-like chamber containing the fire-suppressing material.

For structural support, the fire detection system may include a porous spongy like material, such as open cell foam, where the firmer non-porous component of the spongy material may serve as a supportive structure by which to create an open chamber between the gas sampling inlet system and between the underlying pancake-like chamber containing the fire-suppressing material.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIG. 2A illustrates an isolated right angle connector.

FIG. 2B illustrates two limbs of a circle system breathing circuit connected to an endotracheal tube (ETT).

DETAILED DESCRIPTION OF ILLUSTRATIVE EMBODIMENTS

Figure 1A:
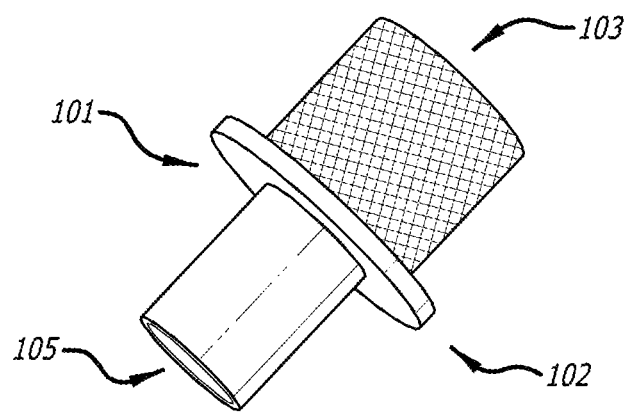
FIG. 1A illustrates a hollow ETT adapter.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

An intelligent, multi-sensor, fire detection and suppression system may preemptively detect an incipient operating room fire in milliseconds. If sensor thresholds are exceeded (indicating an impending fire), the system may initiate fire suppression with a speed that exceeds human reaction times. The system may be based on Fourier Transform Infrared Spectroscopy (FTIR) that detects flames, toxic materials, combustion byproducts, ignitable gases, and smoke particles.

A linear thermistor (temperature-dependent resistor) within an ETT/breathing tube may be used to detect and localize the site of temperature rise. If a threshold is exceeded, a saline jet may be applied to rapidly extinguish the ignited material and thus to suppress the fire. Similarly, a sensor-based system may be used to rapidly detect fires in the operating field. Such an intelligent response system may significantly reduce airway fires, enhance patient safety, and have broad adoption by the medical community.

FTIR Spectroscopy is a single beam interferometry-based technique for the detection of chemical structural fragments within molecules, known as functional groups that tend to absorb infrared radiation. The IR radiation may cause the chemical bonds in the material to vibrate, such that there may be a correlation between the molecule's spectral wave-number and its structure. However, FTIR may not be usable to detect molecules without bonds (single atoms such as helium and monoatomic ions) or symmetrical diatomic molecules (such as $N_2$ and $O_2$), because they may not absorb radiation. However, for $N_2$ and $O_2$, current ICU and operating room monitors are available that may provide instant clinical information about the presence and concentration of these molecules.

For a polyvinyl ETT or other device (e.g., LMA) in the airway, pure polyvinyl chloride may be a rigid solid. Breathing tubes may be made flexible through the addition of plasticizers such as phthalates (as much as 25%). Spectral corrections may be made for water vapor, background, phthalate additives, and the FTIR instrument itself. Gaseous substances may produce narrow spectral bands, and it may be possible to obtain high resolutions of 2 $cm^{-1}$. Other measures may involve use of the Rayleigh criterion and the full-width half-maximum of the spectral peak.

For airway fires, an instrument either internal or external to the airway associated with an ETT/breathing tube may locally sense the presence of an actual or impending fire. The instrument may respond immediately with activation of a saline spray or jet to extinguish the fire, or it may respond with a jet of compressed air or other non-flammable gas to blow out the fire (as in "blowing out a match"). This system may operate automatically. The system response may be made fast (within milliseconds) and effective (instant saline jet or instant jet of air or non-flammable gas), and may complement the OR team response.

A multimodal sensor may be used to detect indications of an imminent or incipient fire. The sensor may be configured with appropriate components to monitor some or all of the following parameters simultaneously:

Temperature: The sensor may be configured to detect an abnormally high temperature, which may indicate the location and extent of the heated region, and of an actual or impending tissue burn.

Flame Detection: The sensor may be configured to detect the presence of the 308 nm signature ultraviolet radiation peak from excited hydroxyl ($OH^-$) molecules seen in flames. This may be accomplished with the use of Fourier Transform Infrared Spectroscopy (FTIR) that identifies molecules by their wavelengths of infrared light at which they absorb.

Ignitable Atmosphere: The sensor may be configured to detect a local inspired gas concentration of alcohol-based vapors and other ignitable vapors, also detected by FTIR.

Toxic Material Detection: The sensor may be configured to use FTIR to detect toxic combustion materials. The principal combustion breakdown products of polyvinyl chloride (PVC) ETT tubes are hydrochloric acid (HCl), carbon dioxide, and carbon monoxide (CO). Other breakdown products in lesser amounts may include benzene, toluene, xylene, and the specific breakdown products of added plasticizers.

Smoke Detection: The sensor may be configured to detect carbonaceous ionized particles that may indicate the presence of smoke, including smoke from human tissue. This may be achieved in conjunction with FTIR by assessing the non-wavelength specific absorption of IR light (which would correspond to absorption of IR by solid particles).

A thermistor may be embedded in the wall of an ETT/breathing tube to generate a change in resistance in response to an altered temperature. The site of temperature rise can be localized and displayed on a screen. This may be accomplished with a series of rings, located in the ETT/breathing tube wall, spaced evenly along the tube length, that are composed of material with temperature-dependent electrical resistivity (e.g., carbon fibers).

FIG. 1A shows a hollow ETT adapter 101 with two ends: a proximal end 103 that may have a standardized 15 mm total diameter, a flange 102, and a distal end 105 that may be inner diameter-specific, i.e., it may be approximately the same diameter as the lumen of the elongated tube portion of the ETT.

Figure 1B:
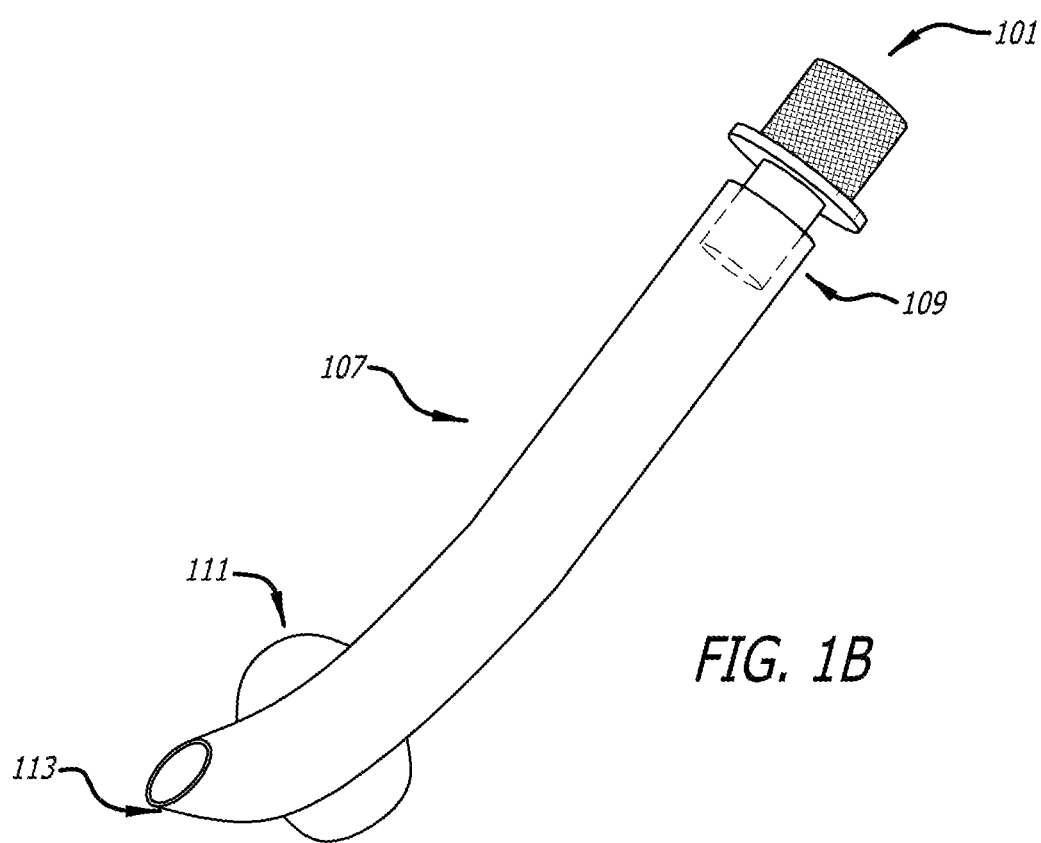
FIG. 1B illustrates a hollow endotracheal tube with its adapter.

FIG. 1B shows a hollow endotracheal tube 107 with a proximal end 109, a distal end 113, and an inflatable balloon cuff 111. The distal end of the adapter 105 may be inserted into the proximal end 109 of the elongated tube of the ETT.

FIG. 2A shows an isolated right angle connector. The right angle connector 201 may have an inlet port 207 for access to the connector's central lumen.

FIG. 2B shows how the two limbs of a circle system breathing circuit (inspiratory limb 203, expiratory limb 205) may come together to create a breathing circuit connector 213 that attaches to the proximal end 211 of a right angle connector 201. The connector's distal end 209 may attach-to the 15 mm diameter ETT adapter. The right angle connector 201 may be inserted between the ETT adapter 101 and the breathing circuit connector. The ETT may include the adapter 101, its elongated tube shaft 107, a distal opening 113, and may include an inflatable balloon 111. The arrows indicate a general path of gas flow.

Figure 3:
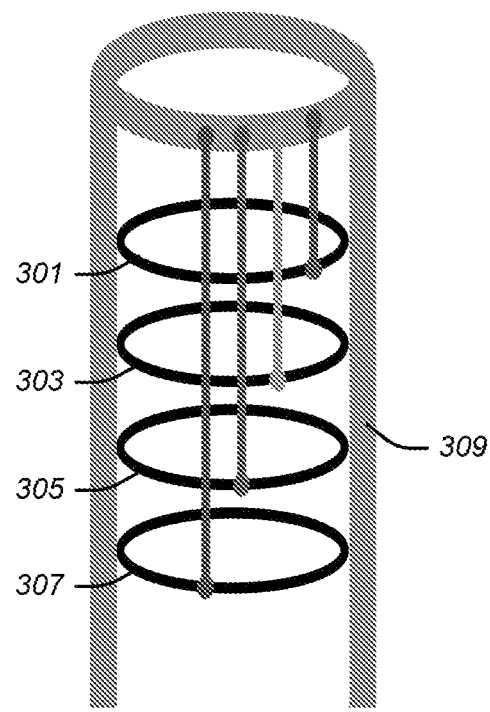
FIG. 3 illustrates a stacked set of rings of thermistor wire on or within an ETT wall.

FIG. 3 illustrates a stacked set of split rings of thermistor wire on or within an ETT wall. As illustrated in FIG. 3, a set of split thermistor wire rings 301, 303, 305, and 307 may be stacked on or within the wall of an ETT 309. The rings may be spaced evenly along the length of the ETT 309. The thermistor wire may be composed of material with temperature-dependent electrical resistivity (e.g., carbon fibers). Each level may have an independent thermistor system consisting of a ring composed of a material having an electrical resistance that changes with temperature and two electrically conducting wires generally oriented parallel to the axis of the tube. One of these electrically conducting wires may be common to all rings. In order for the rings to measure the temperature in their immediate vicinity, the thermal path caused by the electrical wiring and connections may have a thermal resistance that is much greater than the thermal resistance between the undesired heat source or fire and the rings.

An audible and/or visual alarm may be configured to sound whenever any of the threshold criteria for the parameters being monitored are exceeded, or when certain substances are found to be present that indicate a hazardous condition. Messages over a network may also be sent.

Irrigation Response Development

When sensor fire thresholds are exceeded within the lumen of an ETT/breathing tube, the heat-generating surgical instrument being used may instantaneously be deactivated, and a saline jet or spray may be activated to cover and cool the ignited material with a barrier of saline solution and vapor. Cooling may also result from heat loss due to saline's latent heat of vaporization. The surgeon may have the option to manually activate the spray or jet device one or more times at will.

A miniature, multimodal, airway-fire sensing and saline jet or spray-irrigating device may be encased in a fire-resistant, explosion-proof housing. The type and location of the fire sensor/suppressor may depend on the presence or absence of an airway device, such as an ETT/breathing tube, and the type of anesthesia required. Broadly speaking, there may be two major categories to consider: the intubated airway and the non-intubated airway.

When sensor fire thresholds are exceeded within the lumen of an ETT/breathing tube, the heat-generating surgical instrument being used may instantaneously be deactivated, and an instant jet of compressed air or other non-flammable gas may be used to blow out an incipient fire (as in "blowing out a match").

The Intubated Airway

During airway instrumentation with a ventilation device, such as an ETT/breathing tube, there may be two possible regions within which an airway fire can originate—either within the gas pathway that extends throughout the internal lumen of the ETT/breathing tube, or within the region external to the ETT/breathing tube. The region external to the ETT/breathing tube may include the space outside the wall of the ETT/breathing tube, the distal airway beyond the tip of the ETT/breathing tube, and its exposed proximal end attached to an ETT/breathing tube adapter. In principle, a fire can extend from the inner or outer surface into the wall of the ETT/breathing tube, but generally not outwards from within the wall itself.

Fire Inside ETT

If the fire is inside the lumen of the ETT/breathing tube, detection may be with a multimodal sensor attached to the ETT via its I.D.-specific adapter. The adapter's distal lumen may be approximately the diameter of the ETT/breathing tube to which it is attached, and thus may be an ETT/breathing tube inner diameter-specific adapter. However, the proximal end of the I.D.-specific adapter may be standardized to have a 15 mm diameter fitting, by which it connects to the 22 mm diameter fitting of the breathing circuit.

The right angle connector may contain the fire sensing/suppression systems, and it may be attached to the standardized proximal end of the I.D.-specific ETT/breathing adapter.

Figure 4:
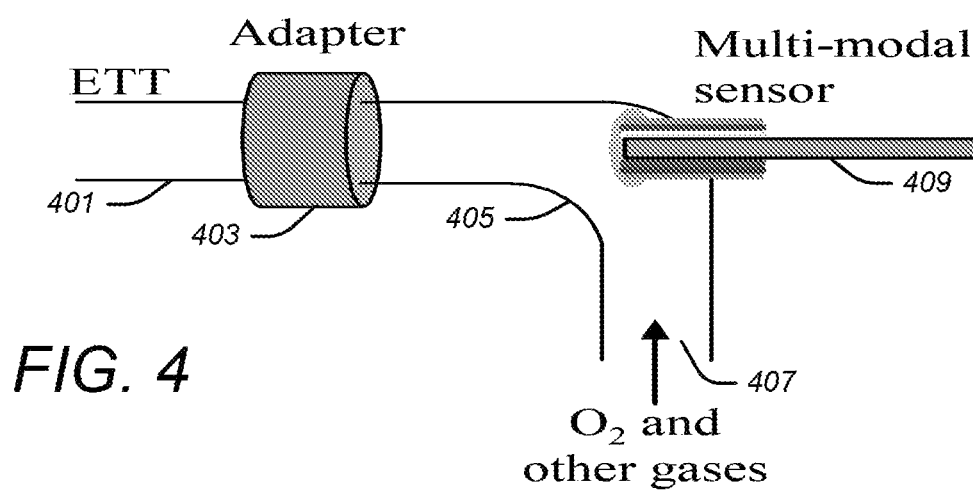
FIG. 4 illustrates a fire detection and suppression system within an elbow connector attached to an endotracheal tube so as to effectuate fire detection and suppression of imminent or incipient fires within the lumen of an endotracheal tube.

FIG. 4 illustrates a fire detection and suppression system mounted in a right angle elbow attached to the I.D.-specific adapter of the ETT/breathing tube so as to effectuate fire detection and suppression of imminent or incipient fires within the lumen of an ETT/breathing tube. As illustrated in FIG. 4, an endotracheal tube 401 may be connected with an adapter 403 to an elbow 405. The elbow 405 may have a substantially right-angle bend which provides an oxygen-carrying gas inlet 407 at a proximal end thereof. The endotracheal tube 401 may have a longitudinal axis which makes an approximately 90 degree or other angle with respect to the longitudinal axis of the gas inlet 407. The fire detection system and fire suppression system 409 may both be configured to receive access to the lumen of the elongated tube at approximately the bend of the elbow. The elbow 405 may be configured as a right angle device, where the fire detection and suppression systems may be pointed directly into the lumen of the ETT, whereas oxygen and other gases may enter and exit through a side port.

Plastic can melt in response to a fire. In order to prevent the device from melting (with consequent misdirection and spillage of the saline jet), the structural integrity of device can be maintained by encasing it with a shield with a high melting point, and composed of either a metallic substance or a Vespel polyimide plastic (500° C. melting point).

Fire Outside ETT

Signs of fire (flames, smoke, etc.) may be external to an instrument (e.g., ETT/breathing tube, rigid/flexible endoscope, bronchoscope) that is inserted through and below the glottis. In such a situation, a fire detection and suppression system may be located throughout the length of the wall of the instrument and may quickly detect fire elements in the sub-glottic and supraglottic regions, as well as outside of the mouth. Within the wall of the instrument, sensing line conduits with outlets that open to the outside may be coated with a layer of metallic material, and made to follow the length of the tube more proximally, so as to converge with the parent sensor channel in the ETT/breathing adapter.

Figure 5:
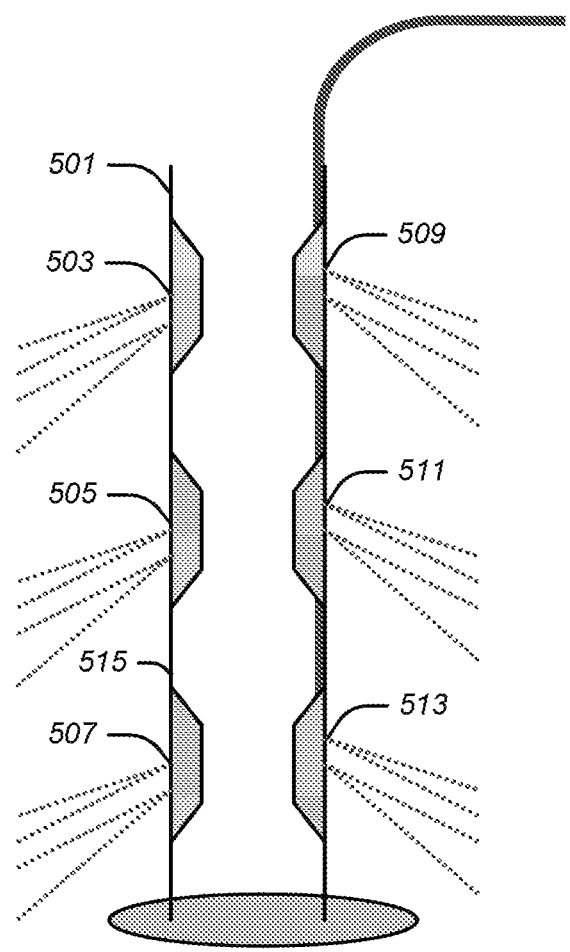
FIG. 5 illustrates a plurality of fluid outlets in the outer wall of an endotracheal tube.

FIG. 5 illustrates a plurality of fluid outlets in the outer wall of an endotracheal tube. As illustrated in FIG. 5, an endotracheal tube 501 may have a plurality of fluid outlets 503, 505, 507, 509, 511, and 513 which may be spaced from one another along a length and circumference of the outer wall 515 of an endotracheal tube 501.

Upon sensor activation due to an imminent or incipient fire, saline irrigation may proceed through multiple thin metal-lined resistant channels (not shown) to the fluid outlets 503, 505, 507, 509, 511, and 513. Valves may not be needed at the outlets because capillary pressure may hold the saline in place, even if no external pressure is applied. The pressure required to push may be sufficient if it exceeds $P=2*S/r$ where S is the surface tension (which may be approximately 0.07 N/m for water) and r is the outlet radius. The irrigation conduits may be separate from sensor-sampling conduits. The conduits may extend throughout the length of the instrument. The protected areas may include the lung, trachea, glottis, pharynx, mouth, and face. Alternatively, the inserted instrument may be covered with a separate disposable protective sheath equipped with sensing/irrigation conduits.

A complete fire detection and suppression system may include: (1) an ETT connector-embedded device to sense/irrigate the inner lumen of the ETT/breathing tube, and (2) a system of sensing-irrigation conduits in the ETT/breathing tube wall, for fires originating outside the ETT/breathing tube wall region. Other instruments may also be equipped with such an outer wall, either intrinsically added or supplemented with an ETT/breathing tube-encasing protective sheath.

This irrigation conduit approach may make the ETT/breathing tube more bulky by increasing the ETT/breathing tube width, as with certain laser-shield specialized ETT types. If bulkiness is undesirable, the device may be made with only a connector-embedded device that only detects and suppresses intra-luminal fires.

Air Jet Ventilator "Blowout" Fire Suppression System

Continuous air can be provided at high gas flow rates to create an extinguishing "blowout" effect, as in the blowing out of a match. For example, it has been shown in tracheal tubes that the flame spread velocity decreases almost linearly with increasing flow rates above 2.5 L/min. With increasing flow, an upper flammability threshold is reached at 20 L/min, above which the tube cannot be ignited nor can a flame be propagated through it. If so, such an approach might be useful if the initial flow rate is higher than 5 L/min; but for a low flow rate, it might worsen the problem.

An air jet ventilator, with its gas outlet within the interior of the ETT connector, may serve as a functional "blowout device" for intraluminal ETT fires. These jet ventilators, available in most operating rooms, may be set up to deliver emergency oxygen and not air in the obstructed airway setting. Switching from an oxygen cylinder to an air-pressurized cylinder may make sense when it is desired to provide less oxidizer to an ongoing airway fire. Alternatively, a non-flammable gas could also be used for this purpose. The activated jet ventilator flows and volumes may have to be pre-determined to minimize the risk of pulmonary barotrauma injury. After each jet ventilator breath, lung exhalation may be passive secondary to lung elastic recoil.

Studies in models and in experimental animals have demonstrated that gas flow through a 16-gauge cannula in response to a driving pressure of 4 bar (58 psi) is approximately equal to 500 ml/sec. This corresponds to a flow rate of 30 L/min. This is well in excess of the jet ventilator 20 L/min cutoff (333 ml/sec), which may prevent tube ignition and flame propagation. In dog studies, it was demonstrated that low-frequency ventilator rates (less than 30 breaths/min) produced peak airway pressures between 20 and 50 cm $H_2O$.

The Smart Drape System

As indicated above, operating room fires may occur due to excess $O_2$ gas accumulating under a surgical drape due to the tenting effect that the drape may create.

Figure 6:
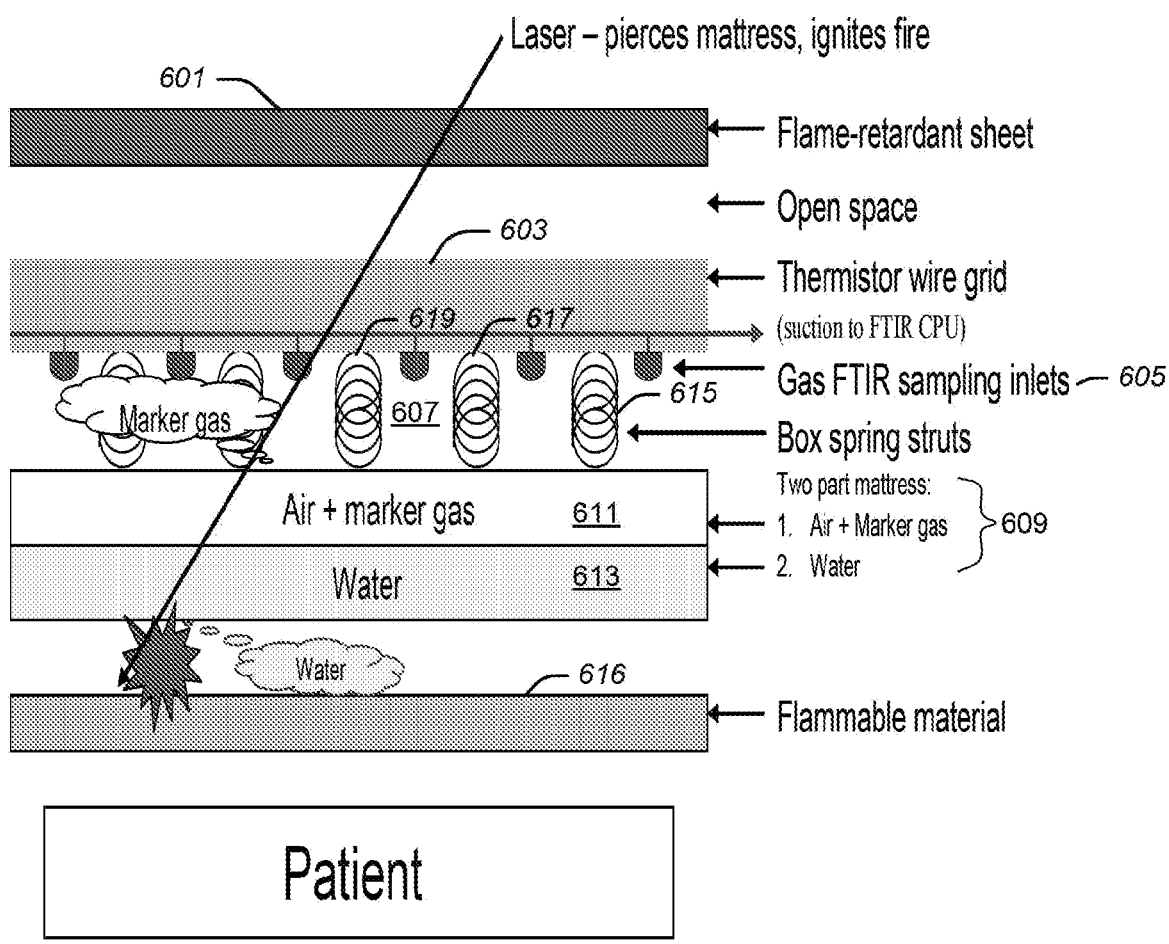
FIG. 6 is a cross-section of a "Smart Drape" multi-layer system that may be used to detect and suppress imminent or incipient fires caused during the use of drapes during surgery.

FIG. 6 is a cross-section of a smart drape system that may be used to detect and suppress imminent or incipient fires caused by the use of a drape during surgery. The layers may consist of a (1) a fire-retardant sheet 601 of surgical drape material, (2) a drape-wide thermistor grid system 603 to localize abnormal temperature rises, (3) a gas sampling line layer 605 containing gas sampling inlets connected to an FTIR fire-detection system, (4) an open space 607 held open by box springs, into which (5) an underlying fire-suppressing mattress layer 609 may release marker gas indicating a breach of the mattress, and which may further release water or saline underneath the mattress onto the patient so as to prevent ignition of patient's clothing or linen, and to suppress any incipient or imminent fire.

The flame-retardant sheet 601 may be made of an ultra-light-weight translucent material that is flame-retardant. For example, the material may be made of polypropylene or poly phenol. However, a laser beam may be able to penetrate the sheet, and may ignite flammable materials underneath it.

The thermistor grid system 603 may be a moldable two-dimensional grid of interconnected, insulated, flexible thermistors that are linked to a central data analyzing processor that monitors the temperature at every point (x,y) in the grid. The grid point values for all (x,y) may be displayed on a screen. The high-temperature points may be colored red, and points in a normal temperature range may be colored green. If a heat-generating instrument causes the temperature at one or more points to rise above a pre-determined threshold, an audible alarm may also be activated that alerts the surgical team to a possible fire.

On its lower surface, the gas inlets may be arranged in a two-dimensional grid and held in place in this grid. Each gas inlet may be connected to a tube that connects the inlet to an FTIR system (e.g., IR light source, detector, mirrors, and Fourier transform data acquisition/data processing) that may be configured to detect smoke, ignitable vapor concentrations from surgical prep solutions, combustion byproducts (HCl, CO, $CO_2$, benzene), and toxic materials. For high concentrations of oxidizer gas underneath the drapes, separate $O_2$ and $N_2O$ sensors may be placed underneath the drape, and may be equipped with audible alarms that are triggered when the sensor thresholds are exceeded.

Sensor thresholds may be established that are indicative of an imminent or incipient fire. When one or more of these thresholds are exceeded, an audible alarm may be triggered. A fire suppression system may in addition or instead be activated which may deliver a jet of saline or other fire-suppression material, or a jet of air or a non-flammable gas, to the area at which the exceeded threshold was detected.

Thus, there may be two types of imminent or incipient fire detection—temperature detection by the thermistor grid wire 603 and gas detection by the gas inlets and associate gas diagnostic system, such as the FTIR system.

The underlying fire-suppressing gas-filled mattress 609 may include a sealed upper pancake-like chamber 611 filled with air and a marker gas attached to a sealed lower pancake-like chamber 613 filled with fire suppression material, such as water. The bottom surface of the lower pancake-like chamber 613 may be in contact with a patient's skin or clothing.

The upper pancake-like chamber 611 may be relatively thin (e.g., ½ inch thick). It may be made of a material which melts under heat, such as polypropylene. If a laser beam penetrates through the upper pancake-like chamber 611, the laser beam may perforate the upper pancake-like chamber 611. This may, in turn, release the marker gas from the upper pancake-like chamber 611 at that location into the narrow space immediately above the upper pancake-like chamber 611. This marker gas may flow into one or more adjoining gas inlets 609 that are connected to a common conduit that leads to the FTIR sensing system. The FTIR system detection of the presence of the marker gas triggers an audible alarm.

An open space or pathway 607 may be created between the overlying intermediate diagnostic gas-sampling layer 605 and the underlying fire-suppressing gas-filled mattress 609, as in FIG. 6. A narrow open space may be required whereby the marker gas released from the underlying fire-suppressing mattress has to traverse only a short distance (e.g., less than 5 mm) in order to enter the intermediate diagnostic layer (with its steady air flow and gas suctioning system), and then conveyed by a common pathway to the FTIR gas analysis system.

This open space layer for gas conveyance, or its equivalent, may be accomplished in different ways, including:

(1) A grid of box spring struts 615, 617, and 619 that physically separates the two layers, and thereby creates an open space, as shown in FIG. 6.

Figure 7:
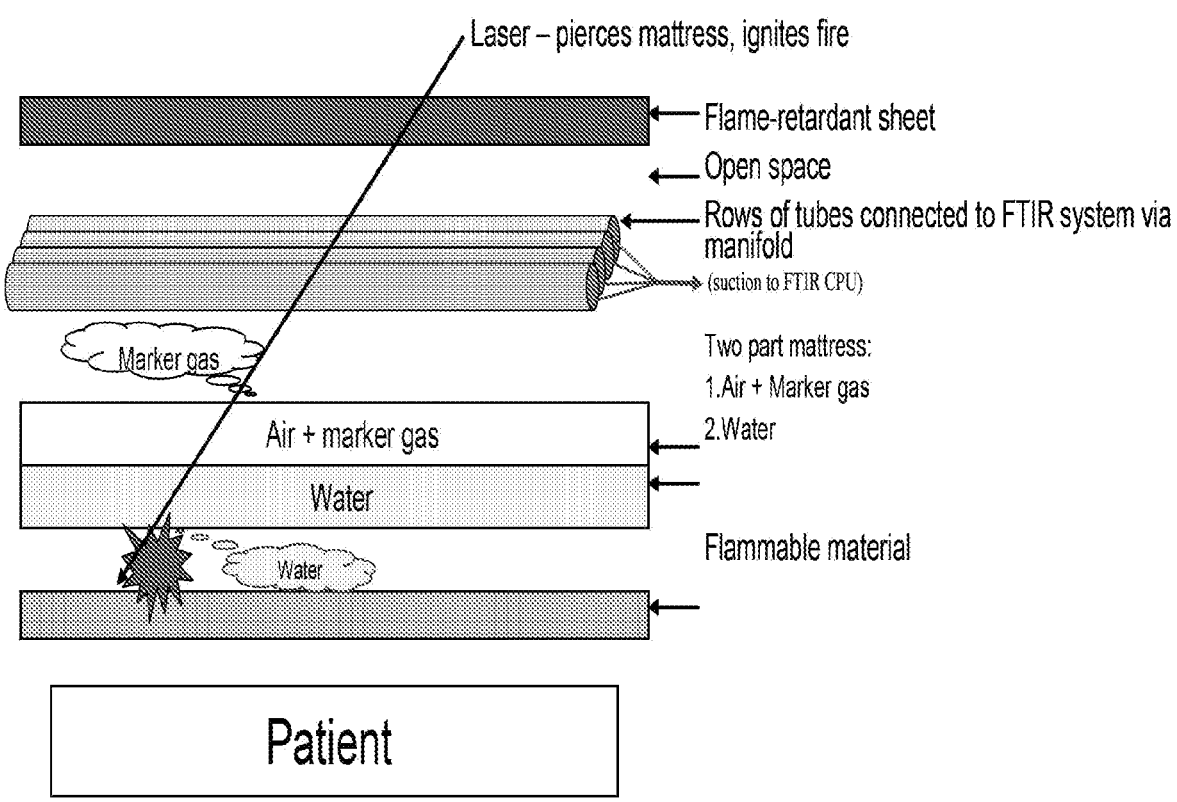
FIG. 7 is another embodiment of a "Smart Drape", with a structure similar to that of FIG. 6, except that the open space is replaced by a manifold of juxtaposed flexible tubes with multiple holes that collects marker gas released from the punctured lower mattress.

(2) Rows of juxtaposed flexible tubes with holes in them, with the tubes connected via a manifold to the gas suctioning system, as shown in FIG. 7 (the other portions of FIG. 7 may be the same as or similar to their corresponding portions in FIG. 6). Such rows of tubes would immediately overly the underlying gas-filled mattress. The holes may provide ready passage of marker gas released from the lower mattress to enter directly into the intermediate diagnostic layer (with its steady air flow and gas suctioning system), and then for the gas to conveyed by a common pathway to the FTIR system. The use of multiple tubes may largely eliminate the need for an open space, and may provide structural support.

Figure 8:
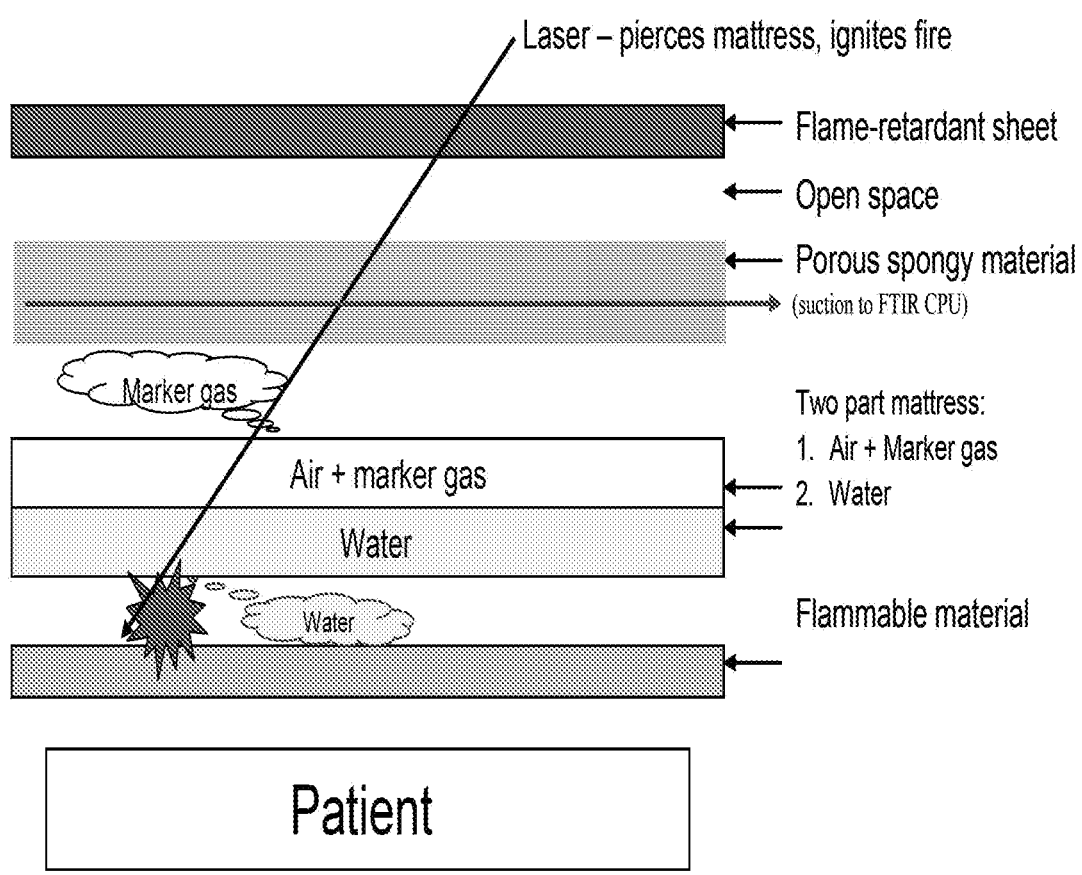
FIG. 8 is another embodiment of a "Smart Drape", with a structure similar to FIG. 6, except that the open space is replaced by a layer of porous spongy material, such as open cell foam, that contains multiple pores that create an open space for the collection of released marker gas.

(3) Porous spongy material, such as open cell foam, which contains multiple pores that create an open pathway between the two layers, and where the physical strut-like separation is achieved by the spongy portion of the material itself, as shown in FIG. 8 (the other portions of FIG. 8 may be the same as or similar to their corresponding portions in FIG. 6).

When the laser beam penetrates through the lower pancake-like chamber 613, it may ignite flammable material 616 below it. However, the laser beam may also perforate the lower pancake-like chamber 613, thus causing the fire-suppression material which it contains to be released onto the flammable material 616 at the location of the laser beam. In turn, this may suppress any imminent or incipient fire.

If the perforation of the lower pancake-like chamber 613 is very tiny or not at all, the leaked fire-suppression material may be inadequate to effect fire suppression. If a fire develops, however, that fire is likely to create a larger hole in the lower pancake-like chamber 613, thus increasing the amount of fire-suppression material that is applied, which may extinguish the fire.

Thus, there may be multiple levels of fire suppression, including an audible alarm when an excessive temperature or marker gas is detected by the thermistor wire grid 603, the release of fire suppression material due to a perforation of the lower pancake-like chamber 613 by a fire-igniting source such as a laser, and the release of fire suppression material due to a perforation of the lower pancake-like chamber 613 by an actual fire beneath it.

A saline irrigation response system may be used instead of or in addition to the water-filled lower pancake-like chamber 613.

The thermistor wire grid 603 may be configured such that it may be warped to create a surgical work site of arbitrary shape. Alternatively, pre-shaped drapes for surgery in specific anatomical regions may be made, e.g., for the head and neck, the torso, and the extremities.

The smart drape system which has been described may also be used to warm a patient's body to prevent hypothermia or other problems.

Experiments

Measurement devices may be used which include: 20 W $CO_2$ laser, IR two-color pyrometer, and a Fourier Transform Infrared Spectrometer. Descriptive statistics may be used. All flame experiments may be videotaped and conducted in a flame hood with maximal safety precautions.

Development of Temperature Sensing System

An infrared two-color pyrometer (Omega OS3753 or similar) may be used to record the local tracheal tube temperature in response to a 20 W $CO_2$ laser beam maintained on a spot for variable time periods (e.g., 15 or 30 secs) until ETT ignition is achieved. The temperature of the laser spot (2 mm) along the ETT exterior and its dropoff with longitudinal distance may be measured. The ETT temperature on its inner side may also be measured. The temperature of the heated gas that reaches the ETT connector may be measured. Since intraluminal flames may spread at a rate of 2-3 cm/sec, a spacing of at least one thermistor per cm may be used. Hence, a minimum of 30 thermistors for a 30 cm long adult ETT may be used.

In 30 PVC ETT tests, the laser may be used to burn a hole in the exterior and cutaway interior of the ETT. The Omega OS 3753 may be used to measure the time to ignition (TTI) and temperature rise (usually PVC flash ignition occurs around 390 degrees C.). PVC tubes resist smoldering, but produce more smoke in the flaming mode.

A needle temperature sensor (a coaxial Omega 5TC needle-shaped thermal sensor approx. 0.034 mm diameter) may protrude directly into the lumen of the adapter, but perpendicular to the gas flow. Another configuration may place it coaxially in the adapter center where it is maintained with spokes.

Newly molded PVC ETTs may be made that contain, within the ETT wall, embedded 40 gauge (0.017 mm diam.) insulated thermistor wire. The initial spacing may be 1 wire/cm along longitudinal shaft of ETT. The thermistor wires may emerge at the proximal end of the ETT, where they may connect to an external temperature sensor with a display screen. The minimal spacing between wall sensors needed to avoid false negatives may be determined empirically, as might occur with a 1-2 mm diameter hot spot.

Thirty (30) newly molded ETTs may be built with ETT wall-embedded thermistor sensors, and may be tested with variable $O_2$ concentrations (e.g., 21%, 50%, 95%) at variable flow rates (2-20 L/min). TTIs may be measured. Temperature time rate of change may be quantified as the respective flames spread past successive ETT wall-embedded sensors, and flame speed can be determined from a videotaping of the time course of the flame spread.

Adapter-Based FTIR Sensing System

A background spectral profile and a baseline FTIR instrument spectral profile may be obtained prior to all fire emulation experiments. The baseline ambient gaseous concentrations of combustion byproducts may be assumed to be zero or exceedingly low. The spectral profiles of heated gaseous samples of pure isolated forms of the combustion components—pure polyvinyl chloride (without plasticizer), hydrochloric acid, carbon monoxide, benzene, and other known components—may be obtained. For ETT tubes with different mixtures of plasticizers, a spectral profile library may be created for each commercial type of ETT type being used.

Smoke concentrations may be calculated according to the reduction in optical density relative to a non-smoke baseline value. Consideration may be given to false positive artifacts that can cause spurious reduction of optical density, e.g., via a mucus plug in the airway.

Thirty (30) PVC ETTs may be equipped with newly molded FTIR-sensing ETT connectors. Each connector may be connected to an air/oxygen source with variable $O_2$ concentrations (e.g., 21%, 50%, 95%) and with variable gas flow rates (e.g., 2-20 L/min). The ETT may be ignited, and a flame may be allowed to develop and spread through the ETT.

The time course of the spectral profile of the mixture may be obtained, and the mixture profile may be compared to the individual component profiles.

For temperature sensors, a goal may be to establish a threshold which, when exceeded, triggers a system fire suppression response within 50 milliseconds. For a laser beam or electrocautery device, a rapid increase in the ETT wall temperature may likely provide the earliest indication of an ETT burn or fire, with localization of the hot spot to within a centimeter. Trigger thresholds may be based on absolute temperature, and on rate of rise of temperature. Studies may compare ETT wall sensors vs. ETT connector-embedded sensors.

In terms of FTIR sensing, a goal may be to achieve an FTIR response decision within two seconds. The number of FTIR scans needed for the earliest reliable identification of the combustion byproducts may be determined. Performance of the FTIR device may be measured by its signal-to-noise (SNR) ratio, i.e., the peak height of a chemical signature in an infrared spectrum relative to the noise level. Generally, the SNR may be 3 times the noise to be considered real. If a spectral feature is less than 3 times as intense as noise, it may be ignored. For a constant resolution, the SNR may be related to the number N of scans added together as follows: SNR is approximately equal to $(N)^{1/2}$. The co-adding of FTIR scans may result in a usable SNR, but the number of scans obtained may be balanced against the short time frame within which a decision must be made as to the presence of an airway fire. The relationship between SNR and the time T involved in obtaining FTIR scans is proportional to $(T)^{1/2}$.

The presence of a detectable flame and/or smoke may be a sufficient condition to trigger a fire suppression response. In the absence of a flame, an airway burn alarm algorithm may be developed on the simultaneous measurement of elevated CO, $CO_2$, and smoke. The presence of toxic vinyl compounds, such as HCl and benzene-like agents, may serve as confirmatory agents of an existing adverse thermal event.

Development of FISS Irrigation Response System (Right Angle Connector-Based & ETT Wall Embedded)

A first iteration prototype for the ETT-right angle connector-based (FIG. 2) and ETT wall-based (FIG. 1) spray/jet irrigation systems may be created. The ETT right angle connector may contain a central coaxial (e.g., 3 mm diameter) device that may rapidly inject a saline jet into the interior of the ETT. Tests may be performed to determine the optimal diameter of the spray device outlet, relative to the diameter of the right angle connector, and taking into account the additional space occupied by other components of the fire-detection system. An empirical formula for fire suppression effectiveness of the right angle connector saline jet (saline volume, injection speed) may be developed based upon sensor temperature, flame/smoke presence, HCl and other byproduct concentrations. Fire suppression effectiveness of the ETT wall-embedded saline irrigation system may be developed, tested, and parameterized, initially with the use of irrigation conduits (e.g., 0.2 to 0.5 mm diameter) with an outlet at every cm along the longitudinal shaft of the ETT.

Fire Emulation Experiments with ETT Right Angle Connector-Based FISS System

Laser-beam/electrocautery induced fire emulations with a right angle connector-based FISS device involving PVC ETTs may be done with 30 ignitable tracheal models with a flammable coating. TTIs, laser lockout, and FISS response time/efficacy may be evaluated.

Development of ETT Wall-Embedded FISS Irrigation Conduit System

Fire emulation experiments may be conducted with 30 intubated ignitable tracheal models using PVC ETTs with complete ETT wall-embedded saline irrigation conduits and outlets. TTIs, laser lockout, and FISS response time/efficacy may be evaluated, and performance problems corrected.

Development of Connector-Based Air Jet Ventilator "Blow-Out" System

Thirty (30) newly molded ETT adapters may be made that contain a right angle connector-embedded temperature sensor as well as a coaxial 16-gauge needle attached to an air jet ventilator. The ETT plus adapter may be connected to a gas source with variable $O_2$ concentrations (e.g., 21%, 50%, 95%) and with variable flow rates (e.g., 2-10 L/min). Upon ETT ignition, videotaped flames may be allowed to spread through the ETT toward the right angle connector. Upon adapter threshold activation, the air jet ventilator may deliver air volume bursts of 300 ml/sec or more up to a maximum 500 ml/sec. For a given $O_2$ concentration, the threshold timing and the fire suppression efficacy of the air volumes may be correlated.

Development of "Smart Drape"

A model system (20 cm×20 cm) for the "Smart Drape" System may be created with five distinct layers: (a) thermistor grid, (b) gas sampling lines connected to an FTIR source, analyzer, and processing unit, (c) narrow air-filled empty space kept open by box spring struts, or replaced by a manifold of hole-filled tubes, or by open cell foam, (d) two-part mattress—the upper part filled with air and marker gas, the lower part filled with water—and (e) flammable clothing material.

Initial experiments may measure on-laser duration vs. rate of thermistor temperature rise. Thermistor grid spacing may be of the order of 1-2 mm, comparable to a spot created by a laser beam. An (x,y) thermistor grid may be created, such that colorized thermistor points are displayed ('red' is hotter, etc). Thermistor wire may be exposed to laser operation for variable time periods (up to 30 sec) to study damage effects (melting, disruption of sensor measurement, and disabling of grid function).

Similarly, the outlets for the FTIR gas sampling lines may be installed in a rectangular grid pattern. An outlet spacing of one every 5 cm for the 20 cm×20 cm grid, i.e., about 15 outlets may initially be used. The plastic sampling outlets may also be tested for laser damage. The total FTIR response time may depend on the gas flow speed from outlet to analyzer, plus the processing time for co-added FTIR scans. Conventional gas sampling flow rates of 100-200 ml/min may initially be used in operating room capnometry devices, and may be modify accordingly. The resolution sensitivity of the FTIR system may be dependent on the presence of significant marker gas concentrations in the open space, which may be challenging in the presence of a small mattress perforation. The marker gas concentration in the mattress may be as high as possible, but, if released in large quantities, the marker gas concentration should not pose any clinical risk of impairing respiratory function in a non-intubated patient. For this reason, non-toxic halocarbons such as $CF_4$ and $C_2F_6$ may be used initially.

With an intact five-layer model system, flammable materials may be tested with a $CO_2$ laser in air and oxygen-enriched environments. These materials may include polyester surgical gowns, cotton towels, and polypropylene surgical drapes. The time to ignition (TTI) of these dried materials may be studied in air, 50% $O_2$, and 100% $O_2$. Primary ignition may be defined as visual observation of the TTI of a single material. Secondary ignition (ST) may be defined as the TTI of a sample of material combined with a promoter, such as cellulose filter paper, that readily ignites. TTI and STI measurements may be made of these materials alone, and then with filter paper placed behind them.

Usage Considerations and Potential Pitfalls

ETT/breathing tubes made of polyvinyl chloride may be the most commonly used airway devices. Hence, a universal FISS system that can be used routinely for all ETT/breathing tubes, and a "Smart Drape" system for generic surgical cases that offers added protection to operating room personnel, may have a greater impact on the incidence of operating room fires than the occasional use of specialized laser-resistant tubes for high risk cases. Some of the FISS features described herein could be extended to existing laser-resistant ETTs.

False negatives may result in significant injury to the patient. If the sensor thresholds are set sufficiently low, it is highly unlikely that a FISS detection system with fast real-time monitoring of fire parameters would fail to detect a fire. False positives would cause unnecessary saline injections into the airway, but these may not be injurious, and may be tolerable provided the total volume is no more than a 200-300 mL (about 10% of an adult lung functional residual capacity). Partial suctioning of the injected saline may be done.

A saline spray in the airway, or a water-soaked drape in the vicinity of the surgical field, could become an electrical hazard when an electrocautery device is used. If the system is designed properly, with an immediate lock-out of the ESU device prior to activation of the saline jet, there should be little concern. The O.R. isolation transformer isolates the electrical power from ground, and sounds an alarm when it detects leakage currents in a secondary circuit that has been grounded. With a unipolar electrocautery device, the generated current may leave through a large skin surface dispersive electrode ("grounding pad"). Electrocautery may be avoided if the surgical field is close to an oxygen source. This may be wise for initial usage of the fire detection and suppression system, until all safety issues are resolved. Bipolar electrocautery device may be safer because current flow is through two small electrodes 1 mm apart, and might not need a dispersive electrode. A coblation RF device may prove to be better in lowering fire risk.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

For example, existing ETT and breathing tubes of all types may be modified to include the any of the temperature and FTIR-based fire detection/fire suppression systems described herein. Current devices that could be thus outfitted include laryngeal mask airways, double-lumen tubes, Combitubes, bronchial blocker tubes, tracheostomy tubes, oral and nasal RAE tubes, and even laser-resistant tubes. All such tubes may have in common the 15 mm male adapter required by ASTM standards.

The temperature and FTIR-based fire detection/fire suppression systems which have been discussed may be used in conjunction with all known manual ventilation devices, types of breathing circuits, and automatic anesthesia/ICU mechanical ventilators. Compatible ventilation systems include manual self-inflating ventilation bags, (e.g., the Ambu bag), the circle system with its inspiratory and expiratory limbs, coaxial tube systems, and Mapleson circuits (A, B, C, D, E, and F).

The fire detection/fire suppression systems described herein for the Smart Drape have been presented herein for use with an immobile patient undergoing operating room surgery. These designs may be extended to the clothing ("drapes") that individuals in motion wear in high-risk situations involving exposure to fire, e.g., firemen, soldiers in combat, and paramedics, as well as those who work regularly in environments with volatile environments (oil rigs, gasoline lines, chemical factories, sugar mill, paper mill).

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials which have been described and their equivalents. Similarly, the phrase "step for" when used in a claim is intended to and should be interpreted to embrace the corresponding acts which have been described and their equivalents. The absence of these phrases in a claim mean that the claim is not intended to and should not be interpreted to be limited to any of the corresponding structures, materials, or acts or to their equivalents.

Nothing which has been stated or illustrated is intended or should be interpreted to cause a dedication of any component, step, feature, object, benefit, advantage, or equivalent to the public, regardless of whether it is recited in the claims.

The scope of protection is limited solely by the claims which now follow. That scope is intended and should be interpreted to be as broad as is consistent with the ordinary meaning of the language which is used in the claims when interpreted in light of this specification and the prosecution history which follows and to encompass all structural and functional equivalents.

The invention claimed is:

1. Apparatus for oxygenating the airway of a patient comprising:
    a device for delivering an oxygen-carrying gas into the airway;
    a fire detection system configured to detect indications of an imminent or incipient fire in the airway; and
    a fire suppression system configured to suppress the imminent or incipient fire in the airway in response to detection of the imminent or incipient fire in the airway by the fire detection system;
    wherein the device for delivering an oxygen-carrying gas is an endotracheal tube or a breathing tube used as a conduit for oxygen delivery to the lung; and
    wherein:
        the fire detection system is configured to detect indications of an imminent or incipient fire within the lumen of the endotracheal or breathing tube; the fire suppression system is configured to suppress the imminent or incipient fire within the lumen of the endotracheal or breathing tube in response to detection of the imminent or incipient fire in the lumen of the endotracheal or breathing tube by the fire detection system; and the apparatus includes: an elbow connector having a substantial right-angle bend which provides an oxygen-carrying gas inlet at a proximal end thereof; and an elongated tube at the other end of the elbow having a longitudinal axis which makes an approximately 90 degree angle with respect to the longitudinal axis of the gas inlet; and the fire detection and suppression systems are configured to both receive access to the lumen of the elongated rube at approximately the bend of the elbow; or
        the fire detection system is configured to detect indications of an imminent or incipient fire outside of the endotracheal or breathing tube; and the fire suppression system is configured to suppress the imminent or incipient fire outside of the endotracheal or breathing tube in response to detection of the imminent or incipient fire outside of the endotracheal or breathing tube by the fire detection system; and the fire detection system includes a thermistor system embedded within the outer wall of the endotracheal or breathing tube and the thermistor system includes a set of spaced-apart and stacked rings of thermistor wire; or the fire suppression system includes a plurality of fluid outlets spaced from one another along a length and circumference of the outer wall of the endotracheal tube.

2. The apparatus of claim 1 wherein:
the fire detection system is configured to detect indications of an imminent or incipient fire within the lumen of the endotracheal or breathing tube; and
the fire suppression system is configured to suppress the imminent or incipient fire within the lumen of the endotracheal or breathing tube in response to detection of the imminent or incipient fire in the lumen of the endotracheal or breathing tube by the fire detection system.

3. The apparatus of claim 2 wherein:
the endotracheal or breathing tube system includes:
   an elbow connector having a substantially right-angle bend which provides an oxygen-carrying gas inlet at a proximal end thereof; and
   an elongated tube at the other end of the elbow having a longitudinal axis which makes an approximately 90 degree angle with respect to the longitudinal axis of the gas inlet; and
the fire detection and suppression systems are configured to both receive access to the lumen of the elongated tube at approximately the bend of the elbow.

4. The apparatus of claim 1 wherein:
the fire detection system is configured to detect indications of an imminent or incipient fire outside of the endotracheal or breathing tube; and
the fire suppression system is configured to suppress the imminent or incipient fire outside of the endotracheal or breathing tube in response to detection of the imminent or incipient fire outside of the endotracheal or breathing tube by the fire detection system.

5. The apparatus of claim 4 wherein the fire detection system includes a thermistor system embedded within the outer wall of the endotracheal or breathing tube.

6. The apparatus of claim 5 wherein the thermistor system includes a set of spaced-apart and stacked rings of thermistor wire.

7. The apparatus of claim 4 wherein the fire suppression system includes a plurality of fluid outlets spaced from one another along a length and circumference of the outer wall of the endotracheal tube.

8. The apparatus of claim 1 wherein the fire suppression system is configured to suppress the imminent or incipient fire in the airway by injecting a blast of non-flammable gas, a jet of liquid saline, or other fire suppressant into the airway, in response to detection of the imminent or incipient fire in the airway by the fire detection system.

9. The apparatus of claim 1 wherein the fire detection system is configured to detect two or more of the following within the airway: a rapid change in temperature, a flame, an ignitable atmosphere, combustion byproducts, toxic materials, and smoke.

10. The apparatus of claim 9 wherein the fire detection system uses Fourier Transform Infrared Spectroscopy to detect at least one of the listed parameters.

11. The apparatus of claim 3 wherein the fire detection and suppression systems are pointed directly into the lumen of the endotracheal tube or a breathing tube.

12. The apparatus of claim 3 further comprising a metallic or Vespel polyimide plastic shield configured to prevent melting of the device in the presence of a fire.

* * * * *